(12) United States Patent
Amemiya et al.

(10) Patent No.: US 6,855,113 B2
(45) Date of Patent: Feb. 15, 2005

(54) DIAGNOSTIC INFORMATION GENERATION APPARATUS AND ULTRASONIC DIAGNOSTIC SYSTEM

(75) Inventors: Shinichi Amemiya, Tokyo (JP); Ryota Ohsumi, Tokyo (JP)

(73) Assignee: GE Medical Systems Global Technologies Company, LLC, Waukesha, WI (US)

( * ) Notice: Subject to any disclaimer, the term of this patent is extended or adjusted under 35 U.S.C. 154(b) by 0 days.

(21) Appl. No.: 10/391,131

(22) Filed: Mar. 18, 2003

(65) Prior Publication Data

US 2003/0181811 A1 Sep. 25, 2003

(30) Foreign Application Priority Data

Mar. 19, 2002 (JP) ........................................ 2002-076284

(51) Int. Cl.[7] .................................................. A61B 8/00
(52) U.S. Cl. ...................................... 600/437; 128/903
(58) Field of Search .................................. 600/437, 443, 600/447; 128/903, 916; 709/213, 230, 231, 232, 247

(56) References Cited

U.S. PATENT DOCUMENTS

| | | | |
|---|---|---|---|
| 4,751,929 A | | 6/1988 | Hayakawa et al. |
| 5,030,953 A | * | 7/1991 | Chiang .................. 341/172 |
| 5,126,962 A | * | 6/1992 | Chiang .................. 364/725 |
| 5,635,645 A | | 6/1997 | Ottes et al. |
| 6,106,472 A | * | 8/2000 | Chiang et al. ............. 600/447 |
| 6,142,946 A | | 11/2000 | Hwang et al. |
| 6,213,944 B1 | * | 4/2001 | Miller et al. .............. 600/437 |
| 6,231,510 B1 | | 5/2001 | Negrin et al. |
| 6,315,722 B1 | | 11/2001 | Yaegashi |
| 6,440,072 B1 | * | 8/2002 | Schuman ................. 600/437 |
| 6,468,217 B1 | * | 10/2002 | Fazioli .................... 600/443 |
| 6,471,649 B1 | * | 10/2002 | Saccardo et al. .......... 600/437 |
| 6,475,146 B1 | * | 11/2002 | Freiburger et al. ......... 600/437 |
| 6,530,887 B1 | * | 3/2003 | Gilbert et al. ............. 600/459 |
| 6,569,097 B1 | * | 5/2003 | McMorrow et al. ........ 600/437 |

FOREIGN PATENT DOCUMENTS

JP 53-108690 9/1978

* cited by examiner

Primary Examiner—Francis J. Jaworski
(74) Attorney, Agent, or Firm—Carl B. Horton, Esq.; Armstrong Teasdale LLP

(57) ABSTRACT

An ultrasonic diagnostic system, which is intended to perform the wireless communication of ultrasonic diagnostic information within the speed range of general-purpose data communication standards, is arranged in a first and second units. The first unit includes ultrasonic wave transmit/receive means which transmits an ultrasonic wave and receives the echo of the wave, data generation means which produces digital diagnostic data based on the received echo, data compression means which compresses the digital data, and data communication means which sends out the compressed data in wireless manner. The second unit includes data communication means which receives the transmitted data, data expansion means which expands the received data, and information generation means which produces display information from the expanded data.

19 Claims, 4 Drawing Sheets

DIAGNOSTIC INFORMATION GENERATION APPARATUS AND ULTRASONIC DIAGNOSTIC SYSTEM

CROSS REFERENCE TO RELATED APPLICATIONS

This application claims the benefit of Japanese Application No. 2002-076284 filed Mar. 19, 2002.

BACKGROUND OF THE INVENTION

The present invention relates to a diagnostic information generation apparatus and an ultrasonic diagnostic system, and particularly to a diagnostic information generation apparatus and ultrasonic diagnostic system which utilize an ultrasonic wave.

An ultrasonic diagnostic system operates to scan the inside of a subject of diagnosis with ultrasonic beams, receive a resulting echo, produce image data based on the strength of echo, and produce a so-called B-mode image. This scheme is also called B-mode imaging.

In addition, the apparatus evaluates the Doppler shift of the echo and produces a color image indicative of the flow velocity distribution of fluid such as blood, i.e., so-called color Doppler image, based on the Doppler shift of echo. The apparatus also produces a color image indicative of the power of Doppler signal, i.e., so-called power Doppler image. The apparatus implements the frequency analysis of the Doppler signal and displays resulting spectra or releases resulting Doppler sound signals. This scheme is also called Doppler diagnosis.

Japanese Patent Unexamined Publication No. S53-108690 discloses a technique of building an ultrasonic diagnostic system in two divided sections. One of the two section is a unit which scans the inside of a subject of diagnosis with ultrasonic beams, receives a resulting echo, and produces diagnostic information from the echo. The other section is a unit which produces display information from the diagnostic information. The diagnostic information is transferred from the one unit to the other unit by wireless communication.

The above-mentioned wireless communication is required to be as fast as around several megabytes/sec in order to keep the real-time performance of diagnosis. Such a high communication speed exceeds overwhelmingly the speed of communication means which are based on general-purpose wireless communication standards such as Bluetooth for example. On this account, general-purpose communication means cannot be used, and a special communication means must be designed.

SUMMARY OF THE INVENTION

Accordingly, it is an object of the present invention to accomplish a diagnostic information generation apparatus which performs the wireless communication for ultrasonic diagnostic information within the speed range of general-purpose data communication standards, and also accomplish an ultrasonic diagnostic system which uses the diagnostic information generation apparatus. In this specification, the wireless communication implies the communication based on the use of radio wave, light, etc. which travels in the space.

(1) The present invention at one viewpoint for solving the foregoing problem resides in a diagnostic information generation apparatus which is characterized by comprising an ultrasonic wave transmit/receive means which transmits an ultrasonic wave and receives the echo of the wave, data generation means which produces digital diagnostic data based on the received echo, data compression means which compresses the digital data, and data communication means which sends out the compressed data in wireless manner.

The invention at this viewpoint is designed to transmit an ultrasonic wave and receive the echo of the wave, produce digital diagnostic data based on the received echo, compress the digital data and send out in wireless manner, whereby it is possible to perform the wireless communication for ultrasonic diagnostic information within the speed range of general-purpose data communication standards.

(2) The present invention at another viewpoint for solving the foregoing problem resides in an ultrasonic diagnostic system arranged in a first section which produces diagnostic information by utilization of ultrasonic wave and a second section which produces display information from the diagnostic information, wherein the first section includes ultrasonic wave transmit/receive means which transmits an ultrasonic wave and receives the echo of the wave, data generation means which produces digital diagnostic data based on the received echo, data compression means which compresses the digital data, and data communication means which sends out the compressed data in wireless manner, and the second section includes data communication means which receives the transmitted data, data expansion means which expands the received data, and information generation means which produces display information from the expanded data.

The invention at this viewpoint is designed to operate on the part of the first section to transmit an ultrasonic wave and receive the echo of the wave, produce digital diagnostic data based on the received echo, compress the digital data, and send out the compressed data in wireless manner, whereby it is possible to perform the wireless communication for ultrasonic diagnostic information within the speed range of general-purpose data communication standards.

It operates on the part of the second section to receive and expand the transmitted data, and produce display information from the expanded data, whereby it is possible to obtain information for real-time display. The released information can be a B-mode image, color Doppler image, power Doppler image, Doppler spectra, Doppler sound, or the like.

The data compression means preferably implements the data compression in compliance with a general-purpose data compression standard, since it is readily available. The general-purpose data compression standard can be JPEG, MPEG, or the like.

The data communication means preferably implements the communication in compliance with a general-purpose data communication standard, since it is readily available.

The data communication means preferably implements the communication based on radio wave, since it is good in terms of information propagation. The data communication standard can be Bluetooth, CDMA2000, IEEE802.11, SWAP, or the like.

The data communication means preferably implements the communication based on light, since it is small in power consumption. The data communication standard can be IrDA, or the like.

The digital data is preferably sonic beam data, so that it minimizes data processing in need before compression.

The sonic beam data is preferably derived from the detection and logarithmic conversion of the signal of received echo, since it is proper for B-mode imaging.

The sonic beam data is preferably derived from the autocorrelation process of the signal of received echo, since it is proper for color Doppler imaging.

The ultrasonic wave transmit/receive-means preferably implements the transmission and reception after the end of communication frame of the data communication means, so that the ultrasonic wave transmission/reception take place in concert with the data communication.

The information generation means preferably converts the coordinates of sonic beam space into the coordinates of real space for the sonic beam data, so that it produces image information which indicates accurately the shape of the subject of imaging.

The first section of the system is preferably a transportable unit, so that it is large in terms of latitude of the site of use.

The second section of the system is preferably a transportable general-purpose information unit, since it is readily available. The information unit can be a portable personal computer, portable information terminal, portable telephone unit, or the like.

According to the present invention, it is possible to accomplish a diagnostic information generation apparatus which performs the wireless communication of ultrasonic diagnostic information within the speed range of general-purpose data communication standards, and an ultrasonic diagnostic system which uses the diagnostic information generation apparatus.

DETAILED DESCRIPTION OF THE INVENTION

Figure 1:
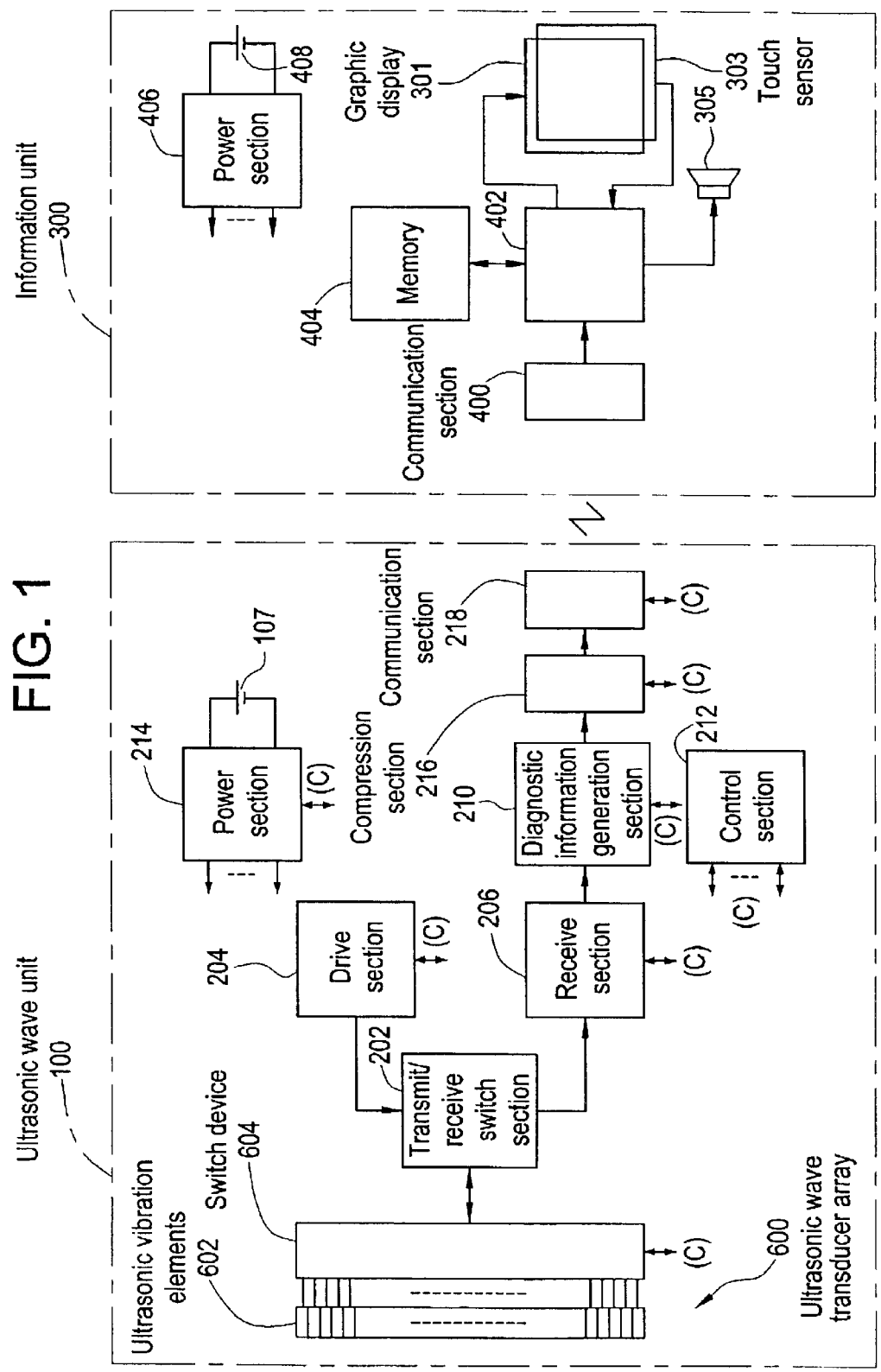
FIG. 1 is a block diagram of an example of embodiment of the system of this invention.

An embodiment of the present invention will be explained in detail with reference to the drawings. FIG. 1 shows a block diagram of an ultrasonic diagnostic system. This system is an embodiment of this invention. The arrangement of this system shows an example of embodiment pertinent to the inventive system.

As shown in the figure, the system is arranged in two units, which are an ultrasonic wave unit 100 and an information unit 300. The ultrasonic wave unit 100 and information unit 300 are an example of embodiment of the first section and second section, respectively, defined by this invention. The ultrasonic wave unit 100 is also an example of embodiment of the inventive diagnostic information generation apparatus. The arrangement of this apparatus shows an example of embodiment pertinent to the inventive diagnostic information generation apparatus.

The ultrasonic wave transducer array 600 is, for example, an arcuate array which is convex toward the radiating direction of ultrasonic wave, i.e., it is a so-called convex array.

The ultrasonic vibration elements 602 of the ultrasonic wave transducer array 600 are connected individually to a switch device 604. The switch device 604 selects a certain number of ultrasonic vibration elements 602 that contribute to ultrasonic wave transmission and reception of the ultrasonic wave transducer array 600. The number of ultrasonic vibration elements 602 to be selected is 16 for example, and this number larger than 1 is arbitrary.

The selected ultrasonic vibration elements 602 of 16 in number, for example, form the aperture for ultrasonic wave transmission/reception. The 16 ultrasonic vibration elements of the aperture are changed in their combination sequentially. Consequently, the aperture moves in steps from one end to another end of the ultrasonic wave transducer array 600. This switching operation takes place under control of a control section 212 which will be explained later.

The ultrasonic wave unit 100 further includes a transmit/receive switch section 202. The transmit/receive switch section 202 is connected with the switch device 604, a drive section 204 and a receive section 206.

The transmit/receive switch section 202 puts drive signals, which are released by the drive section 204, in to the switch device 604 at the time of communication. The number of drive signals corresponds to the number (e.g., 16) of ultrasonic vibration elements 602 of the aperture. Each drive signal is given a phase difference for beam forming of the output ultrasonic wave. The drive signals put in to the switch device 604 are applied to the respective ultrasonic vibration elements 602, which then emit ultrasonic wave beams.

The echo of the ultrasonic wave is received by each corresponding ultrasonic vibration element 602 of the aperture. The transmit/receive switch section 202, at the time of reception, puts a number (e.g., 16) of echo reception signals, which are conducted by the switch device 604, in to the receive section 206. The receive section 206 gives phase differences for beam forming to the echo reception signals and sums the signals, thereby producing an echo reception signal of one sonic beam. The above-mentioned transmit/receive operation is carried out while moving the aperture by the switch device 604.

Figure 2:
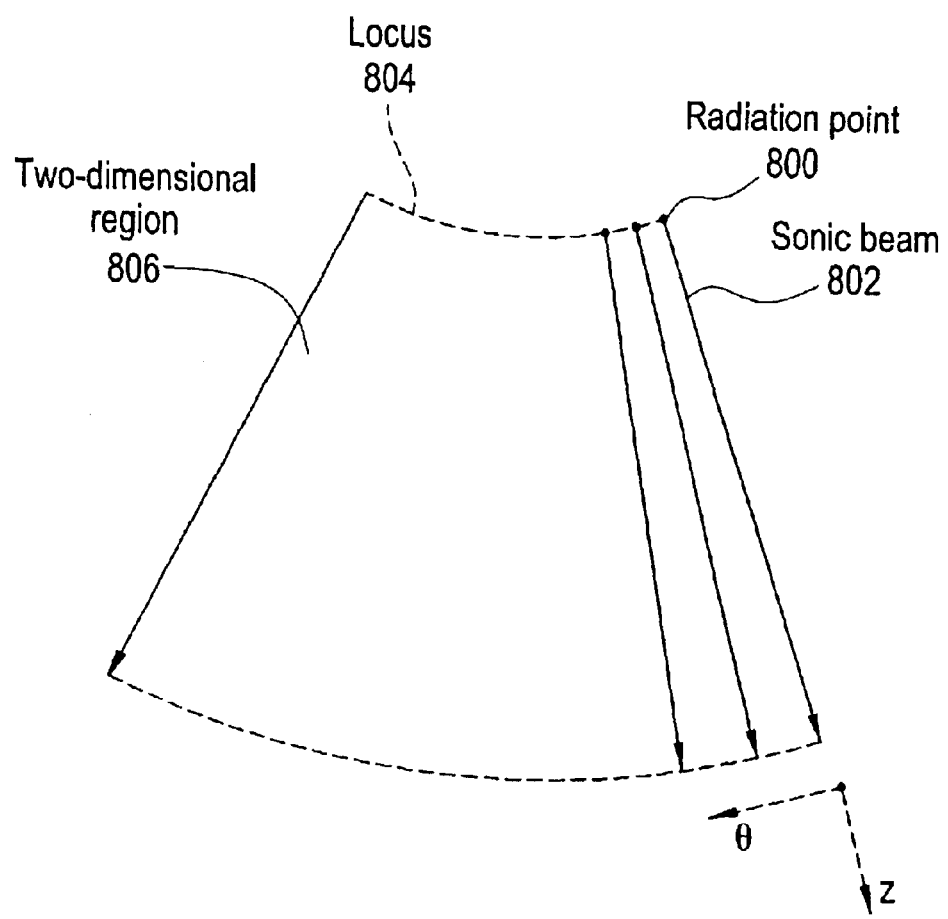
FIG. 2 is a conceptual diagram of sonic beam scanning.

Due to the design of the ultrasonic wave transducer array 600 as a convex array, the radiation point 800 of the sonic beam 802 moves along an arcuate locus 804 to scan a two-dimensional sectoral region 806 at directions θ thereby performing the so-called convex scanning as shown in FIG. 2.

The ultrasonic wave transducer array 600 can be formed arbitrarily, instead of the foregoing arrangement. It may be a two-dimensional array, instead of one-dimensional array. In these cases, the switch device 604, drive section 204 and receive section 206 are arranged to match with the ultrasonic wave transducer array 600.

The echo reception signal produced by the receive section 206 is put in to a diagnostic information generation section 210. The diagnostic information generation section 210 produces digital diagnostic data based on the echo reception signal. The digital diagnostic data is B-mode imaging data for example. B-mode imaging data is produced by detecting the echo reception signal and computing the logarithm of the detected signal. B-mode imaging data is produced for each sonic beam.

Digital diagnostic data may be color Doppler imaging data which is based on the Doppler shift of echo reception signal, instead of B-mode imaging data. Or, it may be Doppler diagnostic data.

Color Doppler imaging data is produced by computing the autocorrelation of the echo reception signal. Color Doppler imaging data is a set of data which express the flow velocity, variance, power, etc. Color Doppler imaging data is also produced for each sonic beam. In the following explanation, data produced for each sonic beam will be termed sonic beam data.

Doppler diagnostic data is data which expresses a spectrum of Doppler signal or data which expresses a Doppler sound. Data of Doppler signal spectrum is produced by the frequency analysis of Doppler signal. Data of Doppler sound is produced by evaluating instantaneous values of Doppler signal.

A compress section 216 implements the data compression for the output data of the diagnostic information generation section 210. Data compression takes place in compliance with a general-purpose data compression standard. Based on the data compression in compliance with a data compression standard, circuit parts of compress section 216 are readily available in the market. The general-purpose data compression standard can be JPEG, MPEG, or the like. Or, it may be MP3 for the compression of Doppler sound data.

Data compression by the compress section 216 takes place for each sonic beam for example. This scheme minimizes the preliminary data processing before compression. Data compression may be designed for two-dimensional data which is a set of multiple sonic beam data. In consequence, efficient compression can take place.

Compressed data is sent out in wireless manner by a communication section 218. The wireless communication uses radio wave for example. The radio wave can go through walls of buildings and the like existing on the course. Accordingly, it is desirable in terms of good information propagation. The wireless communication may use light, e.g., infrared light. Using light is desirable in terms of small power consumption.

The wireless communication takes place in compliance with a general-purpose-data communication standard. Based on the adoption of general-purpose data communication standard, circuit parts of the communication section 218 are readily available in the market. The general-purpose data communication standard can be Bluetooth, CDMA2000, IEEE802.11, SWAP, IrDA, or the like.

These communication standards have data communication speeds of, for example,16 Mbps at maximum in the case of IrDA with the physical layer specifications of version 1.4, and the communication based on data compression readily attains data rates ranging from 2M to several mega-bytes per second in terms of data before compression. Accordingly, it is possible to implement properly the communication of ultrasonic diagnostic data which is required to be a real-time performance.

Transmission and reception of ultrasonic wave take place under control of the control section 212 at the each end of communication of one frame by the communication section 218. In consequence, the ultrasonic wave transmission/reception which is harmonious with communication can be performed.

The ultrasonic wave unit 100 further includes a power section 214. The power section 214 produces the power voltages to be supplied to the sections in the unit 100 based on the conversion of electric power of a battery 107. The power conversion is the DC/DC conversion or the like. The power section 214 is also under control of the control section 212.

The information unit 300 includes a communication section 400. The communication section 400 is the data communication partner of the communication section 218 of the ultrasonic wave unit 100. Both communication sections have communication based on a general-purpose data communication standard.

The information unit 300 further includes a CPU (Central Processing Unit) 402. The CPU 402 has input of reception data from the communication section 400. Reception data is compressed data. The CPU 402 expands compressed data. Data expansion takes place in compliance with a general-purpose compression standard. In consequence, the digital diagnostic data produced by the diagnostic information generation section 210 is restored.

The CPU 402 is connected with a memory 404. The restored digital diagnostic data is stored in the memory 404. The memory 404 also stores programs, based on which the CPU 402 operates. The stored programs include a general-purpose OS, for example, and various application programs which are run under the OS. Among these application programs are programs for ultrasonic diagnosis.

The application programs for ultrasonic diagnosis are designed to produce information to be released from diagnostic data. These programs produce a B-mode image from B-mode imaging data, a color Doppler image and power Doppler image from color Doppler imaging data, and a spectrum image and Doppler sound from digital diagnostic data.

The application programs for ultrasonic diagnosis further include a DSC (Digital Scan Conversion) program. This program converts the coordinates of sonic beam space into the coordinates of real space. Based on this coordinate conversion, a B-mode image, color Doppler image, etc. show correctly the shape of the subject of imaging.

Figure 3:
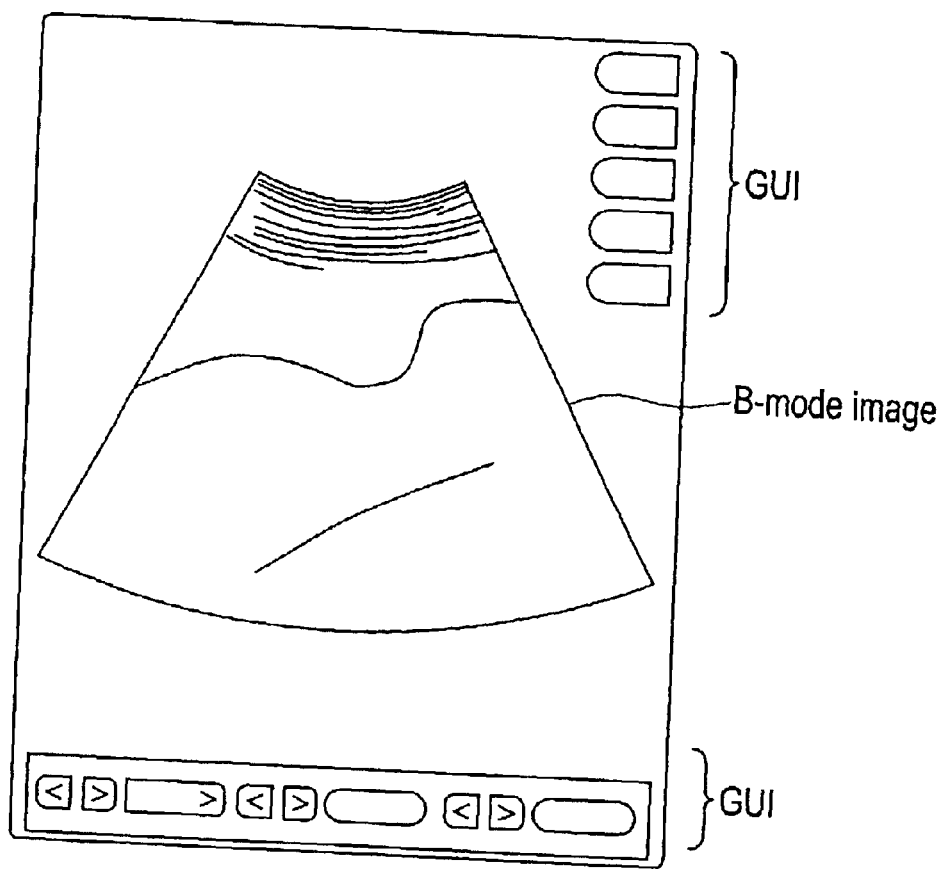
FIG. 3 is a diagram showing briefly an example of image display.

The CPU 402 is further connected with a graphic display 301. The graphic display 301 displays image information released by the CPU 402. FIG. 3 shows an example of display of image information. The figure shows an example of display of a B-mode image. The CPU 402 is further connected with a speaker 305, which releases a Doppler sound.

The graphic display 301 has on its front face a transparent touch sensor 303. The touch sensor 303 is connected to the CPU 402. The touch sensor 303 has its output signal put in to the CPU 402. The user can enter intended operational commands to the CPU 402 by bringing a stylus or the like to comes in contact with the GUI (Graphical User Interface) which is displayed on the graphic display 301. The input section for entering operational commands and the like may be a keyboard in place of the touch sensor.

The information unit 300 has its own power section 406. The power section 406 produces the power voltages to be supplied to the sections in the unit 300 based on the conversion of electric power of a battery 408. The power section 406 is a DC/DC converter or the like.

The ultrasonic wave unit 100 and the information unit 300 are built as separate units. These units can be used in different places within the allowable range of wireless communication. Obviously, these units may be placed closely for use in one place, or may even be integrated. Consequently, this system has a great latitude in terms of place of use.

The ultrasonic wave unit 100 and the information unit 300 are built as transportable units. Consequently, the latitude of the place of use can be fully exerted. In regard to this affair, the portion including the ultrasonic wave transducer array 600 and switch device 604 may be built as an ultrasonic probe separately from the rest of unit 100, with both portions being connected through a signal cable.

The information unit 300 is a general-purpose information unit. The general-purpose information unit is desirable, since it is readily available in the market. The information unit 300 is a portable PC (Personal Computer) for example. Or, it can be a portable PDA (Personal Data Assistant) or a portable telephone unit.

Figure 4:
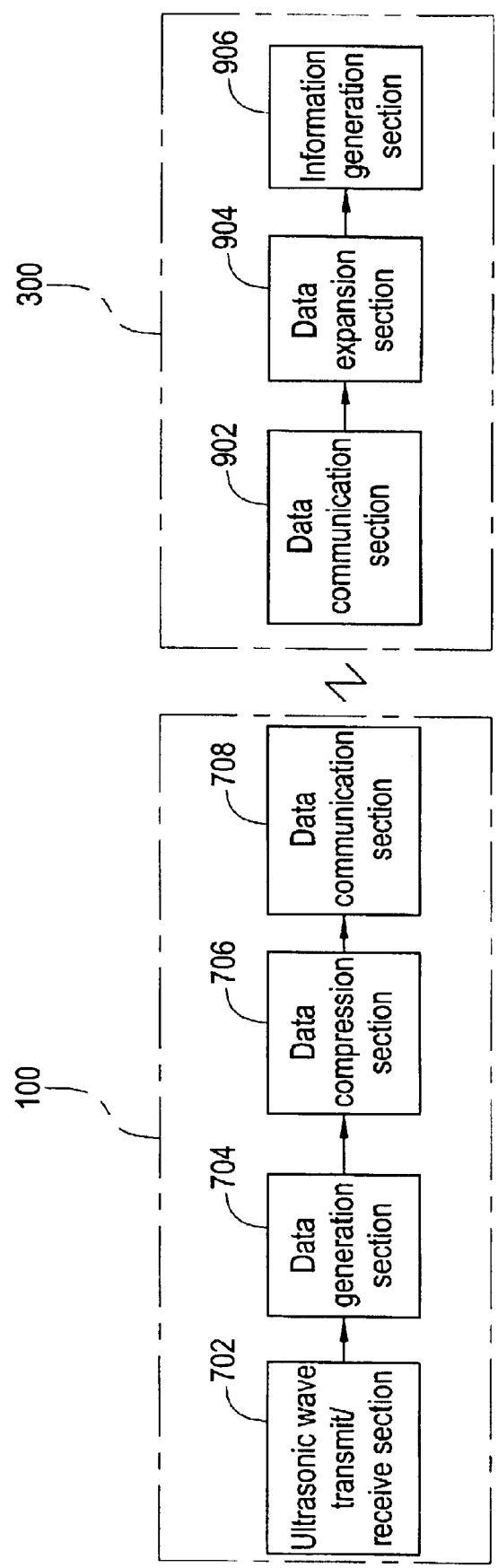
FIG. 4 is a functional block diagram of an example of embodiment of the system of this invention.

FIG. 4 shows a block diagram of this system. As shown in the figure, the ultrasonic wave unit 100 includes an ultrasonic wave transmit/receive section 702, data generation section 704, data compression section 706, and data communication section 708.

The ultrasonic wave transmit/receive section 702 transmits an ultrasonic wave and receives the echo of the wave, and puts the echo reception signal in to the data generation section 704. The ultrasonic wave transmit/receive section 702 is equivalent to the portion including the ultrasonic wave transducer array 600, switch device 604, transmit/receive switch section 202, drive section 204 and receive section 206 explained previously. The ultrasonic wave transmit/receive section 702 is an example of embodiment of the ultrasonic wave transmit/receive means of this invention.

The data generation section 704 produces diagnostic data based on the echo reception signal and puts the data in to the data compression section 706. The data generation section 704 is equivalent to the diagnostic information generation section 210 explained previously. The data generation section 704 is an example of embodiment of the data generation means of this invention.

The data compression section 706 compresses its input data and puts the resulting data in to the data communication section 708. The data compression section 706 is equivalent to the compression section 216 explained previously. The data compression section 706 is an example of embodiment of the data compression means of this invention.

The data communication section 708 sends out its input data. The data communication section 708 is equivalent to the communication section 218 explained previously. The data communication section 708 is an example of embodiment of the data communication means of this invention.

The information unit 300 includes a data communication section 902, data expansion section 904, and information generation section 906. The data communication section 902 puts the received data in to the data expansion section 904. The data communication section 902 is equivalent to the communication section 400 explained previously. The data communication section 902 is an example of embodiment of the data communication means of this invention.

The data expansion section 904 expands its input data and puts the resulting data in to the information generation section 906. The data expansion section 904 is equivalent to the data expansion function of the CPU 402 explained previously. The data expansion section 904 is an example of embodiment of the data expansion means of this invention.

The information generation section 906 produces display information from its input data. The information generation section 906 is equivalent to the display information generation function of the CPU 402 explained previously. The information generation section 906 is an example of embodiment of the information generation means of this invention.

While the present invention has been explained in connection with a preferred embodiment, various alterations and replacements are obviously possible for those skilled in the technical field of this invention without departing from the technical scope of the invention. Therefore, the technical scope of this invention includes not only the foregoing embodiment, but all forms that belongs to the Scope of claim for a Patent.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic diagnostic system comprising:
    an ultrasonic wave transmit/receive device for transmitting a first ultrasonic wave and receiving a first echo of the first ultrasonic wave;
    a data generation device for producing digital diagnostic data based on received echoes including the first echo;
    a data compression device for compressing the digital data;
    a data communication device configured to transmit a first portion of the compressed data corresponding to a first single image frame in wireless manner after a transmission of the first ultrasonic wave and a reception of the first echo by said ultrasonic wave transmit/receive device, wherein said ultrasonic wave transmit/receive device is configured to transmit a second ultrasonic wave and receive a second echo after a transmission of the first portion of the compressed data, and said data communication device configured to transmit a second portion of the compressed data corresponding to a second single image frame after a transmission of the second ultrasonic wave and a reception of the second echo; and
    an information unit for receiving the compressed data and generating information by processing the compressed data.

2. The ultrasonic diagnostic system of claim 1, wherein said data compression device implements the data compression in compliance with a general-purpose data compression standard.

3. The ultrasonic diagnostic system of claim 1, wherein said data communication device implements the data communication in compliance with a general-purpose data communication standard.

4. The ultrasonic diagnostic system of claim 1, wherein said data communication device implements the data communication based on radio wave.

5. The ultrasonic diagnostic system of claim 1, wherein said data communication device implements the data communication based on light.

6. The ultrasonic diagnostic system of claim 1, wherein said digital data is sonic beam data.

7. The ultrasonic diagnostic system of claim 6, wherein said sonic beam data is derived from the detection and logarithmic conversion of a signal of one of the received echoes.

8. The ultrasonic diagnostic system of claim 6, wherein said sonic beam data is derived from the autocorrelation process of a signal of one of the received echoes.

9. An ultrasonic diagnostic system arranged in a first section which produces diagnostic information by utilization of ultrasonic wave and a second section which produces display information from the diagnostic information,
    said first section including:
    an ultrasonic wave transmit/receive device for transmitting first ultrasonic wave and receiving a first echo of the first ultrasonic wave;
    a data generation device for producing digital diagnostic data based on received echoes including the first echo;
    a data compression device for compressing the digital data; and a data communication device configured to transmit a first portion of the compressed data corresponding to a first single image frame in a wireless manner after a transmission of the first ultrasonic wave and a reception of the first echo by said ultrasonic wave transmit/receive device, wherein said ultrasonic wave transmit/receive device is configured to transmit a second ultrasonic wave and receive a second echo after a transmission of the first portion of the compressed data, and said data communication device configured to transmit a second portion of the compressed data corresponding to a second single image frame after a transmission of the second ultrasonic wave and a reception of the second echo; and said second section including:

a data communication device for receiving the compressed data;

a data expansion device for expanding the receive data; and an information generation device for producing display information from the expanded data.

10. The ultrasonic diagnostic system of claim 9, wherein said data compression device implements the data compression in compliance with a general-purpose data compression standard.

11. The ultrasonic diagnostic system of claim 9, wherein said data communication device implements the data communication in compliance with a general-purpose data communication standard.

12. The ultrasonic diagnostic system of claim 9, wherein said data communication device implements the communication based on radio wave.

13. The ultrasonic diagnostic system of claim 9, wherein said data communication device implements the data communication based on light.

14. The ultrasonic diagnostic system of claim 9, wherein said digital data is sonic beam data.

15. The ultrasonic diagnostic system of claim 14, wherein said sonic beam data is derived from the autocorrelation process of a signal of one of the received echoes.

16. The ultrasonic diagnostic system of claim 14, wherein said information generation device converts a first set of coordinates of the sonic beam data in a sonic beam space into a second set of coordinates different than the first set of coordinates.

17. The ultrasonic diagnostic system of claim 9, wherein said first section is a transportable unit.

18. The ultrasonic diagnostic system of claim 9, wherein said second section is a transportable general-purpose information unit.

19. The ultrasonic diagnostic system of claim 1 wherein the information includes at least one of an image and a sound.

* * * * *

UNITED STATES PATENT AND TRADEMARK OFFICE
CERTIFICATE OF CORRECTION

PATENT NO.       : 6,855,113 B2
APPLICATION NO.  : 10/391131
DATED            : February 15, 2005
INVENTOR(S)      : Amemiya et al.

It is certified that error appears in the above-identified patent and that said Letters Patent is hereby corrected as shown below:

In Claim 7, column 8, line 50, after "derived from" delete "the" and insert therefor -- a --.

In Claim 8, column 8, line 54, after "derived from" delete "the" and insert therefor -- an --.

In Claim 9, column 9, line 18, after "expanding the" delete "receive" and insert therefor -- received --.

In Claim 15, column 10, line 12, after "derived from" delete "the" and insert therefor -- an --.

Signed and Sealed this

Second Day of October, 2007

JON W. DUDAS
*Director of the United States Patent and Trademark Office*